US012715913B2

(12) United States Patent
Guo et al.

(10) Patent No.: US 12,715,913 B2
(45) Date of Patent: Aug. 25, 2026

(54) ANTIBODY AGAINST HUMAN THYMIC STROMAL LYMPHOPOIETIN, METHOD AND APPLICATION

(71) Applicant: SHANGHAI MABGEEK BIOTECH. CO., LTD., Shanghai (CN)

(72) Inventors: Jinlin Guo, Shanghai (CN); Yujing Yuan, Shanghai (CN); Wei Dang, Shanghai (CN); Yipan Wu, Shanghai (CN); Lingqiao Zhu, Shanghai (CN); Chenghai Zhang, Shanghai (CN); Qiuling Zou, Shanghai (CN); Zhike Li, Shanghai (CN); Yang Wang, Shanghai (CN)

(73) Assignee: SHANGHAI MABGEEK BIOTECH. CO., LTD., Shanghai (CN)

( * ) Notice: Subject to any disclaimer, the term of this patent is extended or adjusted under 35 U.S.C. 154(b) by 631 days.

(21) Appl. No.: 18/252,146

(22) PCT Filed: Oct. 19, 2021

(86) PCT No.: PCT/CN2021/124560
§ 371 (c)(1),
(2) Date: May 8, 2023

(87) PCT Pub. No.: WO2022/095689
PCT Pub. Date: May 12, 2022

(65) Prior Publication Data

US 2024/0262904 A1 Aug. 8, 2024

(30) Foreign Application Priority Data

Nov. 6, 2020 (CN) ........................ 202011228688.0

(51) Int. Cl.
*C07K 16/24* (2006.01)

(52) U.S. Cl.
CPC ........ *C07K 16/244* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2014/0302061 A1 | 10/2014 | Beaumont et al. | |
| 2017/0066823 A1* | 3/2017 | Edwards .............. | C07K 16/244 |

FOREIGN PATENT DOCUMENTS

| | | |
|---|---|---|
| AU | 2014277673 A1 | 1/2015 |
| CN | 101389657 A | 3/2009 |
| CN | 101809035 A | 8/2010 |
| CN | 108350070 A | 7/2018 |
| CN | 109206514 A | 1/2019 |
| CN | 111196850 A | 5/2020 |
| WO | 2009035577 A1 | 3/2009 |

OTHER PUBLICATIONS

Almagro & Fransson, Frontiers in Bioscience 2008; 13:1619-33 (Year: 2008).*

International Search Report and Written Opinion issued for International Patent Application No. PCT/CN2021/124560, Date of mailing: Jan. 7, 2022, 20 pages including English translation.

Xu, M. et al., "Expression of thymic stromal lymphopoietin in nasal mucosa of a mouse model with allergic rhinitis," J Clin Otorhinolaryngol Head Neck Surg (China), Sep. 2009, vol. 23, No. 17, 3 pages. (English abstract; cited during examination of CN priority application No. 202011228688.0).

Nakajima, S. et al., "Anti-TSLP antibodies: Targeting a master regulator of type 2 immune responses," Allergology International 69 (2020) 197-203 (Cited during examination of CN priority application No. 202011228688.0).

Supplementary Partial European Search Report and Provisional Opinion issued for European Patent Application No. 21888386.6, dated Jan. 15, 2025, 13 pages.

* cited by examiner

*Primary Examiner* — Peter J Reddig
(74) *Attorney, Agent, or Firm* — HSML P.C.

(57) ABSTRACT

Disclosed in the present invention are an antibody capable of binding to human thymic stromal lymphopoietin (hTSLP), a preparation method therefor and an application thereof. The anti-hTSLP antibody of the present invention can specifically bind to a hTSLP receptor, has a good effect of inhibiting the secretion of TARC by PBMC, and can be applied to the treatment of TSLP-related diseases, such as immune-mediated inflammatory diseases.

15 Claims, 2 Drawing Sheets

Specification includes a Sequence Listing.

ANTIBODY AGAINST HUMAN THYMIC STROMAL LYMPHOPOIETIN, METHOD AND APPLICATION

TECHNICAL FIELD

The present disclosure relates to an antibody against human thymic stromal lymphopoietin (hTSLP), especially a neutralizing antibody against hTSLP activity. It further relates to a use of a hTSLP antibody for diagnosing or treating hTSLP-related diseases, wherein for example, the diseases are asthma, chronic obstructive pulmonary disease, atopic dermatitis, allergic rhinitis, fibrosis, inflammatory bowel disease and Hodgkin lymphoma.

BACKGROUND

Bronchial asthma (abbreviated as Asthma) is one of the most common chronic diseases. The incidence rate of asthma has increased year by year worldwide in recent years. At present, there are at least 300 million asthma patients in the world, and about 30 million asthma patients in China. According to the epidemiological data of asthma in Asia, the incidence rate of asthma in adults in Asia is 0.7%~11.9%, with an average of no more than 5% and are increasing in recent years. Current standard therapy for asthma is an inhaled corticosteroid+/−long-acting β-2 agonist, with strong side effects and a probability of causing immune system disorders. Besides, 5-10% of patients currently have no effective drug for treatment. According to the latest data from the China Asthma Epidemiological Survey, only 40.5% of asthma patients in China have been managed. The market urgently needs drugs with strong specificity, low toxic side effects and effective symptomatic management of diseases.

Human thymic stromal lymphopoietin (hTSLP) is a human interleukin-7 (hIL-7)-like cytokine that initiates allergic reactions by stimulating denritic cells (DC), hTSLP is a 159-amino acid protein with 43% homology to mouse TSLP, and comprises a signaling sequence of 28 residues, 6 cysteines, and 2 putative N-glycosylation sites. Non-denaturing sodium dodecyl sulfate polyacrylamide gel electrophoresis (SDS-PAGE) analysis shows the expression of a 23 kilodalton (kDa) protein, while the calculated mature protein molecular weight was 14.9 kDa, indicating that hTSLP is glycosylated. hTSLP contains 7 basic C-terminal amino acids and 6 cysteines that may be involved in the formation of disulfide bonds. The TSLP receptor complex is a heterodimer consisting of TSLP receptor (TSLPR) and IL-7 receptor α (IL-7Rα) chain. Receptors are mainly expressed on monocytes, bone marrow-derived DCs, and B lymphocytes.

TSLP is an epithelial cell-derived cytokine in response to environmental and pro-inflammatory stimuli, which can cause activation of multiple inflammatory cells and downstream pathways. TSLP is increased in the airways of asthmatic patients and is associated with the expression of Th2 cytokine and chemokine and disease severity, Although TSLP is important for the regulation of Th2 immunity, it may also play a key role in other inflammatory pathways and is therefore associated with a variety of asthma phenotypes.

Antibodies could bind target antigens with high affinities, inhibit the activation of receptors by ligands and efficiently block downstream signaling. There is no antibody targeting the TSLP signaling pathway on sale in the world. Preliminary clinical studies have shown that anti-TSLP antibodies are expected to be widely used in the treatment of severe persistent asthma, and patients with different blood eosinophil counts or other Th2 biomarkers have shown the same efficient responses. The present disclosure developed and obtained TSLP antibodies with high affinity by using high-throughput method of hybridoma screening, with higher biological activities than that of other antibodies for the same target, which is expected to be further developed to provide new treatment options for asthma patients at home and abroad.

SUMMARY OF THE INVENTION

In the present disclosure, after a large number of experiments, the inventors obtained a group of monoclonal antibodies that can specifically block the binding of TSLP to TSLP receptors on the cell surface, thereby blocking TSLP signaling and TSLP-mediated biological activities.

In the first aspect, the application provides an antibody or antigen-binding fragment thereof that specially binds to human TSLP, comprising a heavy chain variable region, wherein the heavy chain variable chain comprises an HCDR3 sequence, optionally further comprises an HCDR1 and/or an HCDR2 sequence. In some embodiments, the HCDR3 sequence mentioned above comprises an amino acid sequence selected from SEQ ID NOs: 3, 6, 9 and 12. In some embodiments, the HCDR2 sequence mentioned above comprises an amino acid sequence selected from SEQ ID NOs: 2, 5, 8 and 11. In some embodiments, the HCDR1 sequence mentioned above comprises an amino acid sequence selected from SEQ ID NOs: 1, 4, 7 and 10.

In some embodiments, the heavy chain variable region mentioned above comprises an amino acid sequence with at least 80% homology to the amino acid sequence selected from SEQ ID NOs: 26, 32, 38 and 44, or the heavy chain variable region comprises an amino acid sequence selected from SEQ ID NOs: 26, 32, 38 and 44.

In some embodiments, the antibody or antigen-binding fragment thereof further comprises a light chain variable region, wherein the light chain variable region comprises LCDR1, LCDR2 and/or LCDR3 sequences. In some embodiments, the LCDR1 sequence comprises an amino acid sequence selected from SEQ ID NOs: 13, 16, 19 and 22. In some embodiments, the LCDR2 sequence comprises an amino acid sequence selected from SEQ ID NOs: 14, 17, 20 and 23. In some embodiments, the LCDR3 sequence comprises an amino acid sequence selected from SEQ ID NOs: 15, 18, 21 and 24.

In some embodiments, the light chain variable region mentioned above comprises an amino acid sequence with at least 80% homology to the amino acid sequence selected from SEQ ID NOs: 29, 35, 41 and 47 or the light chain variable region comprises the amino acid sequence selected from SEQ ID NOs: 29, 35, 41 and 47.

In some embodiments, the heavy chain of the antibody or antigen-binding fragment thereof that specially binds to human TSLP comprises an amino acid sequence selected from SEQ ID NOs: 27, 33, 39 and 45 or an amino acid sequence with at least 80% homology to the above sequences. Optionally, the light chain of the antibody or antigen-binding fragment thereof comprises an amino acid sequence selected from SEQ ID NOs: 30, 36, 42 and 48 or an amino acid sequence with at least 80% homology to the above sequences.

In an optional embodiment, the antigen-binding fragment mentioned above is selected from the group consisting of Fab, Fab', F(ab')2, Fv, scFv, Fd fragments and single-chain antibodies. In some embodiments, the antibody that specially binds to human TSLP in the first aspect is a murine monoclonal antibody.

In some embodiments, the antibody that specially binds to human TSLP in the first aspect is a humanized antibody.

In some embodiments, the antibody or antigen-binding fragment thereof disclosed herein is able to inhibit TSLP-dependent STAT5 activation. In another embodiment, the antibody or antigen-binding fragment thereof is capable of inhibiting the secretion of TARC by PBMC.

In the second aspect, the application provides a nucleotide molecule encoding the antibody or antigen-binding fragment thereof that specially binds to human TSLP mentioned above.

In the third aspect, the application provides an expression vector, wherein the expression vector comprises the nucleotide molecule mentioned above.

In some embodiments, the expression vector is pTT5, pUC57, pDR1, pcDNA3.1(−), pDHFF or pCHO 1.0, etc.

In the fourth aspect, the application provides a host cell, wherein the host cell comprises the expression vector mentioned above. In some embodiments, the host cell is HEK293, COS, CHO, NS0, sf9, sf21, DH5α, BL21(DE3) or TG1, etc.

In the fifth aspect, the application provides a method for preparing the antibody or antigen-binding fragment thereof that specially binds to human TSLP in the first aspect, wherein the method comprises the following steps:

a) culturing the host cells in the fourth aspect under an expression condition that allows the host cells to produce the antibody or antigen-binding fragment thereof, thereby expressing the antibody or antigen-binding fragment thereof; and
b) isolating and purifying the antibody or antigen-binding fragment thereof expressed in a).

In the sixth aspect, the application provides a pharmaceutical composition, wherein the pharmaceutical composition comprises the antibody or antigen-binding fragment thereof that specially binds to human TSLP in the first aspect and pharmaceutically acceptable carriers.

In some embodiments, the composition is used for treating human TSLP-related diseases.

In some embodiments, the TSLP-related diseases are selected from asthma, chronic obstructive pulmonary disease, atopic dermatitis, allergic rhinitis, fibrosis, inflammatory bowel disease and Hodgkin lymphoma.

In other aspects, the application provides a method for preventing or treating human TSLP-related diseases, comprising administering to a subject in need the antibody or antigen-binding fragment thereof in the first aspect, or the pharmaceutical composition in the sixth aspect.

In the present disclosure, the anti-human TSLP antibody or antigen-binding fragment thereof can specifically bind to human TSLP, with one or more of the following effects: blocking the binding of human TSLP to hTSLPR; inhibiting TSLP-dependent STAT5 activation; inhibiting the secretion of TARC by PBMC. In the present disclosure, the anti-human TSLP antibody or antigen-binding fragment thereof can be used for preventing or treating TSLP-related diseases, such as immune-mediated inflammatory diseases.

EMBODIMENTS

Figure 1:
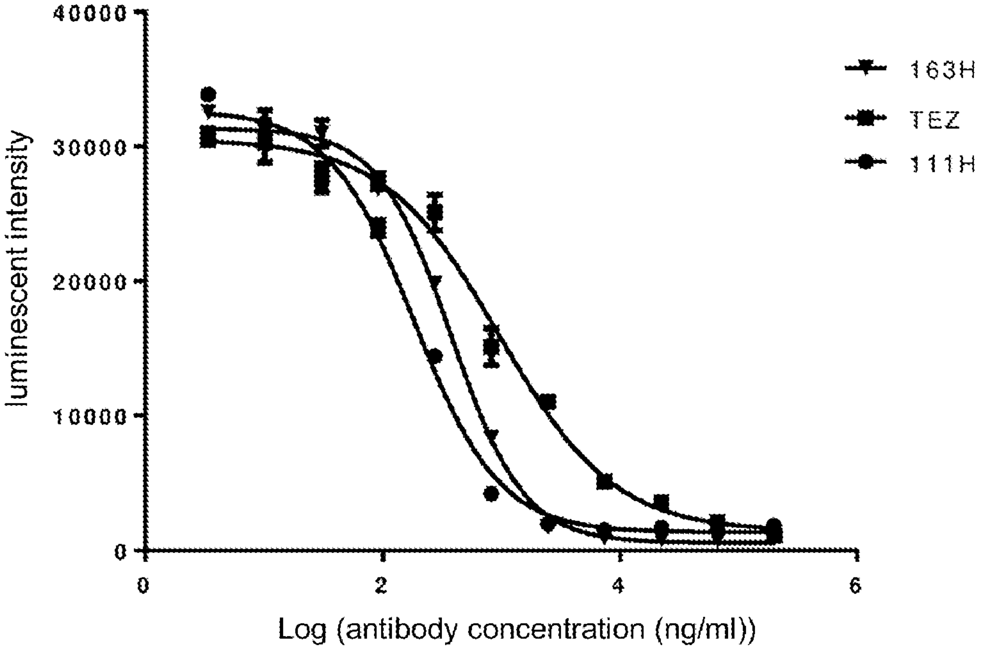
FIG. 1 shows the inhibition of TSLP-dependent STAT5 activation by humanized anti-human TSLP monoclonal antibody.
Figure 2:
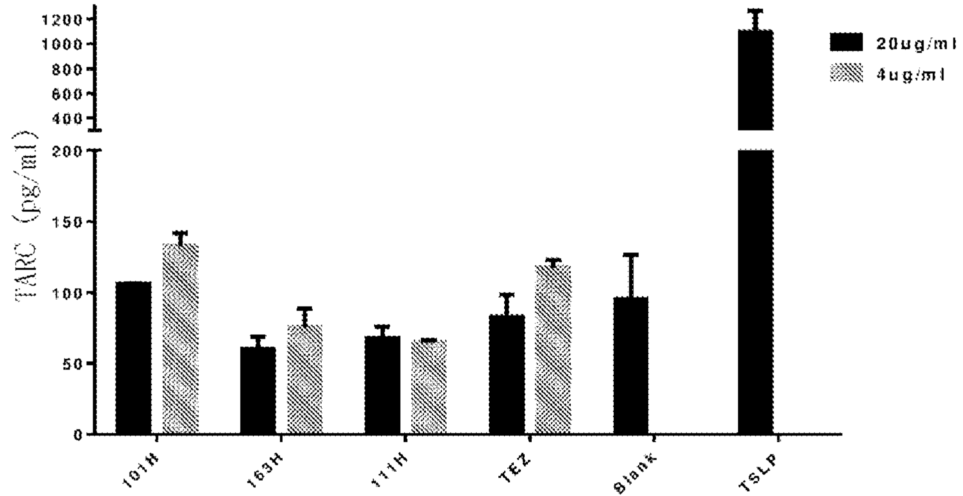
FIG. 2 shows the effects of humanized anti-human TSLP monoclonal antibody in inhibiting the secretion of TARC by PBMC.

The present application provides a novel anti-hTSLP antibody or antigen-binding fragment thereof that specially binds to human TSLP. In a preferred embodiment, the anti-hTSLP antibody or antigen-binding fragment thereof in the present application binds to human TSLP with high affinity and inhibits binding activities between TSLP and TSLPR. The present application also provides a polynucleotide encoding the antibody or antigen-binding fragment thereof, a vector comprising the polynucleotide, a host cell comprising the polynucleotide or vector, a method for preparing and purifying the antibody, and medical and biological uses of the antibody or antigen-binding fragment thereof, such as the prevention or treatment of TSLP-related diseases or conditions. The present application also comprises a method for detecting hTSLP and regulating hTSLP activities using the antibody or antigen-binding fragment thereof.

For easily understanding the present application, certain terms used herein are first defined.

As used herein, the term "antibody" refers to an immunoglobulin molecule comprising four polypeptide chains, namely two heavy (H) chains and two light chains (L) interconnected by disulfide bonds, and their polymers (e.g., IgM). Each heavy chain comprises a heavy chain variable region (abbreviated as VH) and a heavy chain constant region (abbreviated as CH). The heavy chain constant region comprises three domains, CH1, CH2 and CH3. Each light chain comprises a light chain variable region (abbreviated as VL) and a light chain constant region (abbreviated as CL). The light chain constant region comprises a domain (CL1). VH and VL regions can be further subdivided into hypervariable regions called complementary deterministic regions (CDRs), interspersed with conserved regions called framework regions (FR).

As used herein, the term "antigen-binding fragment" of an antibody refers to a fragment or segment of an intact antibody responsible for binding an antigen. An antigen-binding domain can comprise a heavy chain variable region (VH), a light chain variable region (VL) or both. The antigen-binding fragment of the antibody can be prepared from intact antibodies using any suitable standard methods, including proteolytic digestion or recombinant genetic engineering methods. Non-restrictive examples of antigen-binding fragments comprise: Fab fragments; F(ab')2 fragments; Fd fragments; Fv fragments; single-stranded Fv (scFv) molecules; single-domain antibodies; dAb fragments and minimal identification units consisting of amino acid residues that mimic hypervariable regions of the antibody (e.g., isolated CDR). The term "antigen-binding fragment" also comprises other engineered molecules such as diabodies, triabodies, tetrabodies and nanobodies, etc.

As used herein, the term "heavy chain variable region (VH)" and the term "light chain variable region (VL)" respectively refers to a variable heavy chain and light chain region of an antibody, comprising FR1, 2, 3 and 4 and CDR 1, 2 and 3.

Those skilled in the art know that complementary determining regions (CDRs, usually CDR1, CDR2 and CDR3) are the regions in the variable regions with greatest influence on affinity and specificity of the antibody. There are two common ways to define CDR sequences for VH or VL, the kabat definition and the Chothia definition, e.g. see Kabat et al, "Sequences of Proteins of Immunological Interest", National Institutes of Health, Bethesda, Md. (1991); Al-Lazikani et al., J. Mol. Biol. 273:927-948(1997); and Martin et al., Proc. Natl. Acad. Sci. USA 86:9268-9272 (1989). For the variable region sequences of a given antibody, the sequences of CDR region in VH and VL can be determined according to the Kabat definition or the Chothia definition. In an embodiment of the present application, the CDR sequence is defined by Kabat. As used herein, CDR1, CDR2 and CDR3 in the heavy chain variable region refers to as HCDR1, HCDR2 and HCDR3, respectively. CDR1, CDR2 and CDR3 in the light chain variable region refers to as LCDR1, LCDR2 and LCDR3, respectively.

For the variable region sequence of a given antibody, the CDR sequences in the variable region can be analyzed in a variety of ways, for example, by the online software Abysis (http://www.abysis.org/).

As used herein, the term "specifically binding" refers to a non-random binding between two molecules, for example, the binding of an antibody to an epitope of an antigen, for example, the binding of an antibody to a specific antigen with higher affinity of at least twice than that to a nonspecific antigen. However, it should be understood that the antibody can specifically bind to two or more antigens associated with its sequence. For example, antibodies in the present disclosure may specifically bind to human TSLP and non-human (e.g., mouse or non-human primate) TSLP.

As used herein, the term "monoclonal antibody" refers to an antibody obtained from a substantially homogeneous population of antibodies, that is, the antibodies comprised in the population are identical except for possible naturally occurring mutations that may be present in minor amounts. The monoclonal antibody used herein comprise, in particular, a "chimeric" antibody, wherein a fragment of the heavy chain and/or light chain is identical or homologous to the corresponding sequence derived from a particular species in an antibody or belonging to a specific antibody class or subclass, and the remainder of the heavy chain and/or light chain is identical or homologous to the corresponding sequence derived from another species in an antibody or belonging to another antibody class or subclass, and also comprise fragments of such antibodies, provided that they exhibit the desired biological activity (see, U.S. Pat. No. 4,816,567; and Morrison et al., Proc. Natl. Acad. Sci. USA 81:6851-6855 (1984)).

As used herein, the term "homology" is defined as the percentage of identical residues in the amino acid or nucleotide sequence variant after sequence alignment and introduction of gaps, if desired, the maximum percentage of homology. Methods and computer programs used for alignment are well known in the art. As used herein, "at least 80% homology" refers to any value with homology of 80% to 100%, such as 85%, 90%, 95%, 99%, etc.

As used herein, the term "TSLP-related diseases" comprise diseases and/or conditions associated with the activation of TSLP signaling pathway. Examples comprise asthma, chronic obstructive pulmonary disease, atopic dermatitis, allergic rhinitis, fibrosis, inflammatory bowel disease and Hodgkin lymphoma.

In one aspect, the application provides an antibody or antigen-binding fragment thereof that specifically binds to human TSLP, comprising a heavy chain variable region and/or a light chain variable region. The amino acid sequences of CDR, VH, VL, heavy chain and light chain and corresponding nucleotide sequences applicable to the antibodies described in the present application are listed in the following Tables 3-6.

In a specific embodiment, HCDR3 is selected from the amino acid sequence shown in SEQ ID NOs: 3, 6, 9 and 12. In another specific embodiment, HCDR3 is selected from the amino acid sequence shown in SEQ ID NOs: 6, 9 and 12. In a preferred embodiment, HCDR3 is selected from the amino acid sequence shown in SEQ ID NOs: 9 and 12.

In a specific embodiment, HCDR2 is selected from the amino acid sequence shown in SEQ ID NOs: 2, 5, 8 and 11. In another specific embodiment, HCDR2 is selected from the amino acid sequence shown in SEQ ID NOs: 5, 8 and 11. In a preferred embodiment, HCDR2 is selected from the amino acid sequence shown in SEQ ID NOs: 8 and 11.

In a specific embodiment, HCDR1 is selected from the amino acid sequence shown in SEQ ID NOs: 1, 4, 7 and 10. In another specific embodiment, HCDR1 is selected from the amino acid sequence shown in SEQ ID NOs: 4, 7 and 10. In a preferred embodiment, HCDR1 is selected from the amino acid sequence shown in SEQ ID NOs: 7 and 10.

In some embodiments, the heavy chain variable region of the antibody described herein comprises an amino acid sequence selected from SEQ ID NOs: 26, 32, 38 and 44. In a specific embodiment, the heavy chain variable region consists of an amino acid sequence selected from SEQ ID NOs: 26, 32, 38 and 44.

The antibody or antigen-binding fragment thereof described herein may further comprise a light chain variable region in addition to the heavy chain variable region.

In some embodiments, the CDR3 of the light chain variable region (LCDR3) is selected from the amino acid sequence shown in SEQ ID NOs: 15, 18, 21 and 24, or the amino acid sequence shown in SEQ ID NOs: 18, 21 and 24. In a preferred embodiment, LCDR3 is selected from the amino acid sequence shown in SEQ ID NOs: 21 and 24.

In some embodiments, LCDR2 is selected from the amino acid sequence shown in SEQ ID NOs: 14, 17, 20 and 23, or the amino acid sequence shown in SEQ ID NOs: 17, 20 and 23. In a preferred embodiment, LCDR2 is selected from the amino acid sequence shown in SEQ ID NOs: 20 and 23.

In some embodiments, LCDR1 is selected from the amino acid sequence shown in SEQ ID NOs: 13, 16, 19 and 22, or the amino acid sequence shown in SEQ ID NOs: 16, 19 and 22. In a preferred embodiment, LCDR1 is selected from the amino acid sequence shown in SEQ ID NOs: 19 and 22.

In some embodiments, the light chain variable region of the antibody described herein comprises an amino acid sequence selected from SEQ ID NOs: 29, 35, 41 and 47. In a specific embodiment, the light chain variable region consists of an amino acid sequence selected from SEQ ID NOs: 29, 35, 41 and 47.

In some embodiments, the heavy chain or heavy chain variable region, light chain or light chain variable region of the antibody described herein may be formed by substitution, deletion or addition of at least one amino acid residue on the basis of the corresponding specific amino acid sequences listed above and the resulting variant still maintains the activity of binding human TSLP. In some embodiments, the number of above amino acid substitutions, deletions or additions is 1-30, preferably 1-20, more preferably 1-10. In a preferred embodiment, the sequence variant differs from the original amino acid sequence by approximately 1, 2, 3, 4, 5, 6, 7, 8, 9, or 10 amino acids by substitution, deletion and/or addition. In a preferred embodiment, the sequence variant differs from the original amino acid sequence by approximately 1, 2, 3, 4 or 5 amino acids by substitution, deletion and/or addition. In a specific embodiment, the amino acid substitutions are conservative substitutions.

In a preferred embodiment, the antibody described herein is antibody 111H or 163H, wherein the heavy chain sequence of antibody 111H is shown in SEQ ID NO:39 and the light chain sequence is shown in SEQ ID NO:42, wherein the LCDR sequence is identical to antibody 111, HCDR1 and HCDR3 are identical to antibody 111 and the HCDR2 sequence is preferably SEQ ID NO:49; The heavy chain sequence of antibody 163H is shown in SEQ ID NO:45 and the light chain sequence is shown in SEQ ID NO:48, wherein the CDR sequences are identical to antibody 163.

In some embodiments, the antibodies described herein are monoclonal antibodies. In a specific embodiment, the antibodies described herein are humanized antibodies.

The antibody or antigen-binding fragment thereof described herein is capable of specifically binding human TSLP. In a specific embodiment, the antibody or antigen-binding fragment thereof specifically binds to human TSLP or cynomolgus monkey TSLP. In a preferred embodiment, the antibody or antigen-binding fragment thereof specifically binds to human TSLP.

In some embodiments, the antibody or antigen-binding fragment thereof described herein blocks the binding of human TSLP to hTSLPR; inhibits TSLP-dependent STAT5 activation; and inhibits the secretion of TARC by PBMC.

The present application also provides a nucleotide molecule encoding the antibody or antigen-binding fragment thereof described herein, an expression vector comprising the polynucleotide, a host cell comprising the polynucleotide or expression vector, and a method for preparing and purifying the antibody.

In some embodiments, the nucleotide molecule encoding the antibody or antigen-binding fragment thereof is operably linked to a regulatory sequence, and the regulatory sequence can be recognized by the host cell transformed with the expression vector.

In some embodiments, any suitable expression vector may be used in the present application. For example, the expression vector may be one of pTT5, pUC57, pDR1, pcDNA3.1 (+), pDHFF and pCHO 1.0. Expression vectors may comprise fused DNA sequences linked with appropriate regulatory sequences for transcription and translation.

In some embodiments, available host cells are cells comprising the above expression vectors, wherein the host cells may be eukaryotic cells. For example, mammalian or insect host cell culture systems may be used for the expression of the antibodies or antigen-binding fragments thereof. For example, HEK293 cells, COS, CHO, NS0, sf9 and sf21 may be used in the present disclosure. The host cell may also be a prokaryotic cell comprising above expression vector, for example, DH5α, BL21(DE3) or TG1 and so on.

In some embodiments, the preparation method of anti-human TSLP monoclonal antibody described herein comprises: culturing the host cells under a condition that allows expression, thereby expressing anti-human TSLP monoclonal antibodies; and isolating and purifying the expressed anti-human TSLP monoclonal antibodies. With the above method, the recombinant protein can be purified into a substantially homogeneous substance, such as a single band on SDS-PAGE electrophoresis.

In some embodiments, the anti-TSLP antibody described herein can be isolated and purified by affinity chromatography. According to the characteristics of the utilized affinity column, conventional methods such as high salt buffer, changing pH and the like can be used to elute the anti-TSLP antibody bound to the affinity column.

In some embodiments, the humanized anti-human TSLP monoclonal antibody disclosed herein is obtained by the following method: using laboratory-prepared human TSLP antigen to immunize Balb/c mice, after multiple immunization mice with high titers, mouse splenocytes and hybridoma cells are fused for screening hybridoma cell lines with inhibitory TSLP functional activities. More specifically, the inventors of the present application firstly expressed human TSLP antigen respectively through a large number of experiments, then mixed different adjuvants with human TSLP antigen to immunize mice on this basis, and further fused the splenocytes of the above mice with hybridoma cell line sp2/0. Fused hybridoma cells were screened for positive cell lines by using human TSLP antigens. After verifying its functions in blocking human TSLPR binding and inhibiting TSLP, the target cell line was obtained. After humanization of the target molecule, light chain and heavy chain genes were cloned simultaneously into the eukaryotic expression vector pCHO1.0. The above expression vectors were transfected with CHO cells by liposome method and then positive cell clones were screened with puromycin and methotrexate. High-expressive clones were expanded with serum-free medium and humanized anti-human TSLP monoclonal antibodies were isolated or purified with Protein A affinity columns.

In some other embodiments, conventional techniques in the art may be used, for example, PCR mutagenesis to further alter murine parent antibodies to produce chimeric or humanized antibodies or other variants. The parent antibody of the present application may produce a mutant antibody by mutagenesis, for example, in the antigen complementary determining region (CDR) domain for screening target characteristics, such as binding affinity (lower KD), IC50, specificity, preferential binding and so on. Preferably, the target characteristics in mutant antibodies are improved relative to that in the parent antibodies. Mutant antibodies with amino acids substituted are preferred. Besides, at least 1, 2, 3, 4, 5, 6, 7, 8, 9 or 10 amino acid residues of the parent antibody are removed and different residues are inserted at the corresponding positions. The position of the most interest for alternative mutagenesis is one or more CDR regions, but frame region (FR) changes are also considered. Preferably, the substitution is conserved amino acid substitution. Non-conserved amino acid changes can also be introduced for obtaining mutant antibodies, which is used for screening target characteristics.

In some embodiments, Fc modification of the antibody can be used for increasing serum half-life of the antibody. Known mutation sites that can improve the binding ability of human FcRn to antibodies mainly comprise T250Q, M252Y, S254T, T256E, V308P, M428L, N434A, N434S. In the present embodiment, mutations of amino acids at these sites can help to achieve the extension of the serum half-life of antibodies. By Fc modification of the antibodies, ADCC activities can be reduced. Reported mutation sites in Fc region mainly comprise L234A, L235A, L234F and L235E. In the present embodiment, ADCC effects can be reduced by mutations of amino acids at these sites.

The present application provides a pharmaceutical composition comprising an antibody or antigen-binding fragment thereof described herein and a pharmaceutically acceptable carrier. Above-mentioned anti-TSLP antibodies described herein, such as anti-human TSLP monoclonal antibodies, can be formulated with pharmaceutically acceptable carriers into pharmaceutical formulations to exert efficacy more stably. In some embodiments, these formulations may ensure the integrity of core amino acid sequences of the anti-TSLP antibodies described herein, such as anti-human TSLP monoclonal antibodies and also protect multifunctional groups of the proteins from degradation (comprising, but not limited to, agglomeration, deamidation or oxidation). In some embodiments, for liquid formulations, they are generally stable for at least one year at 2° C.-8° C. In some embodiments, for lyophilized preparations, they remain stable at 30° C. for at least six months.

In some embodiments, the anti-human TSLP monoclonal antibody preparations may be suspensions, water needles, lyophilizations and other preparations that are commonly used in the pharmaceutical field, preferably water needles or lyophilized preparations. For water needles or lyophilized preparations of the anti-human TSLP monoclonal antibodies described herein, pharmaceutically acceptable excipients comprise but are not limited to: surfactants, solution stabilizers, isotonic modulators and buffers or combinations thereof. In some embodiments, surfactants comprise but are not limited to: nonionic surfactants such as polyoxyethylene sorbitan fatty acid ester (Tween 20 or 80), poloxamer (such as poloxamer 188), Triton, sodium dodecyl sulfate (SDS), sodium lauryl sulfate, tetradecyl sarcosine, oleyl sarcosine or octadecyl sarcosine, Pluronics, MONAQUAT™, etc. The amount of added surfactants should minimize the granulation of anti-human TSLP monoclonal antibodies. In some embodiments, solution stabilizers include, but are not limited to, one of the following group or combinations thereof: sugars, such as reducing sugars and non-reducing sugars; amino acids, such as monosodium glutamate or histidine; alcohols, such as trialcohols, high-grade sugar alcohols, propylene glycol, polyethylene glycol, etc. The solution stabilizer is added in such an amount that the resulting formulation remains stable for a period of time considered stable by those skilled in the art. Isotonic modulators comprises but are not limited to sodium chloride, mannitol, or combinations thereof. Buffers comprise but are not limited to: Tris, histidine buffer, phosphate buffer, or combinations thereof.

The present application also provides a method for preventing or treating TSLP-related diseases, which comprises administering individual anti-human TSLP antibodies, or compositions comprising anti-human TSLP monoclonal antibodies. In some embodiments, after administration to animals, including humans, the effects of anti-immune-mediated inflammatory response is obvious. Specifically, the anti-human TSLP antibodies described herein are effective in preventing and/or treating immune-mediated inflammatory responses and can be used as anti-inflammatory drugs.

The present application also provides a use of anti-human TSLP antibodies, or compositions comprising anti-human TSLP antibodies, in the manufacture of a medicament for preventing or treating human TSLP-related diseases or symptoms. In some embodiments, the human TSLP-related diseases or symptoms are immune-mediated inflammatory responses or immune-mediated inflammatory diseases.

In some embodiments, the immune-mediated inflammatory responses or immune-mediated inflammatory diseases comprise but not limited to: asthma, chronic obstructive pulmonary disease, atopic dermatitis, allergic rhinitis, fibrosis, inflammatory bowel disease and Hodgkin lymphoma.

In some embodiments, the anti-human TSLP antibodies described herein may be used as drugs for anti-immune-mediated inflammatory responses. In the present application, the drugs for anti-immune-mediated inflammatory responses refer to drugs suppressing and/or treating immune-mediated inflammatory responses, for example, it may delay the development of symptoms related to immune-mediated inflammatory responses and/or reduce the severity of these symptoms. In some embodiments, the drugs may reduce the symptoms accompanying the pre-existing inflammatory responses and prevent the occurrence of other symptoms. In some embodiments, the drugs may also reduce or prevent the transformation of inflammatory responses.

When the anti-human TSLP monoclonal antibodies and compositions thereof described herein are administered to animals including humans, the dose of administration varies with the age and weight of patients, the characteristics and severity of diseases and the route of administration. The dose may refer to the results and comprehensive conditions of animal experiments, with the total dose remaining in a certain range.

The dose and dose frequency of antibodies or compositions thereof may vary depending on the prevention or treatment of the diseases. In prophylactic application, a composition comprising antibodies or combinations thereof of the present application is administered to a patient who is not yet in a disease state to enhance the patient's resistance. This amount is defined as a "prophylactically effective amount". In this use, the specific dose depends on the patient's health status and systemic immunity. Usually, relatively lower doses are administered at relatively infrequent intervals for a longer period of time. In therapeutic applications, it is sometimes necessary to administer relatively higher doses at relatively shorter intervals until the progression of disease is slowed or terminated, and preferably until the patient shows partial or complete improvement of symptoms. After that, prophylactic protocols can be administered to the patient. The specific dose and frequency can be easily adjusted as desired by those skilled in the art.

In this description and claims, the terms "comprising", "containing" and "including" mean "comprising but not limited to" and are not intended to exclude other parts, additives, components, or steps.

It should be understood that the features, characteristics, components or steps described in particular aspects, embodiments, or examples of the present application may be applied to any other aspect, embodiment or example described herein, unless contradicted therein.

The above disclosure generally describes the present disclosure. The following specific examples are further descriptions of the present disclosure and should not be understood as limitations of the present disclosure. Examples do not include detailed descriptions of traditionally conventional methods. Such methods are well known to those skilled in the art and are described in many publications, such as Molecular Cloning Manuals, Experimental Guide to Antibody Technology in Cold Spring Harbor Press. The reagents not indicated by the manufacturer are all conventional reagents.

EXAMPLES

Example 1 Preparation of Human TSLP Antigen Tagged with hFc and Flag, Reference Antibod Tezepelumab and Human TSLP Receptor Extracellular Fragments Tagged with hFc The human TSLP antigen sequence derived from UniProt (UniProtKB-Q969D9), were codon optimized according to the preference characteristics of codon usage in *Homo sapiens*, with a fragment of N-terminal amino acids at positions 29-159 synthesized and subcloned into the pUC57 vector to obtain pUC57-hTSLP. The hFc fragment and the Flag tag (DYKDDDDK, SEQ ID NO: 50) were inserted into the C-terminal of the hTSLP fragment by PCR, constructed into the pTT5 expression vector (laboratory preservation) to obtain pTT5 (hTSLP-hFc) and pTT5 (hTSLP-Flag), and then sequenced. Clones with perfectly correct sequences were selected for plasmid extraction and transfection.

Amino acid sequence of Tezepelumab was derived from IMGT. After codon optimization, the nucleotide sequences of the heavy chain variable region and light chain were synthesized. The heavy chain variable region was firstly connected to the constant region of IgG2 by PCR, cloned into the pTT5 expression vector With the light chain sequence also cloned to the pTT5 expression vector. These sequences were verified by sequencing and plasmid extractions were performed for transfection.

The human TSLPR sequence derived from UniProt (UniProtKB-Q9HC73), were codon optimized according to the preference characteristics of codon usage in *Homo sapiens*, with a fragment of N-terminal amino acids at positions 23-231 synthesized and subcloned into the pUC57 vector. The hFc fragment and the Flag tag (DYKDDDDK, SEQ ID NO: 50) were inserted into the C-terminal of the hTSLPR-ECD fragment by PCR, constructed into the pTT5 expression vector, and then sequenced. Clones with perfectly correct sequences were selected for transfection.

Plasmids were transfected into the HEK293E cell line (laboratory preservation) by PEI. After culturing for 5 days by Freestyle293 medium (purchased from Gibco) containing 3 mM valproic acid, the proteins of interest were purified from cell culture supernatant using Protein A affinity chromatography (purchased from Pharmacia) or Flag affinity chromatography (purchased from Genscript). The quantification of proteins was carried out by the Bicinchoninic acid (BCA) method, with purified proteins used for further analysis and research below. Purified proteins were used for the following mouse immunization, further analysis and research.

Example 2 hTSLP-hFc Immunization

100 μg/mouse of hTSLP-hFc antigen was diluted into 75 μl with normal saline, mixed with an equal volume of Freund's complete adjuvant, and completely emulsified by ultrasonication, with multi-point subcutaneous injection of 4-5 weeks-old Balb/c mice (purchased from Shanghai Lingchang Biotechnology Co., Ltd., animal production license number: SCXK (Shanghai) 2013-0018). After three weeks, 50 μg/mouse of proteins were similarly diluted into 75 μl and mixed with an equal volume of Freund's incomplete adjuvant, and completely emulsified by ultrasonication, with multi-point subcutaneous injection of mice. This immunization was repeated two weeks later. Serums of all mice were separated by tail cutting one week after the third immunization and serum titers were detected using ELISAs coated with hTSLP-hFc antigens. For mice with serum antibody titer>10000, rush immunization was performed one week after blood collection: tail vein injection of 10 μg antigen/100 μl normal saline/mouse.

The titer was detected by ELISA: the ELISA plate was coated with hTSLP-hFc antigen at a concentration of 1 μg/ml, 100 μl per well, overnight at 4° C. The plate was washed with PBST (PBS containing 0.5% Tween-20) twice and drained by patting. 200 μl of coating blocking solution containing 1% BSA was added to each well, blocked at room temperature for 4 hours, drained by patting, and stored in a −20° C. freezer for use. 20 μl of mouse serum of different concentrations were added to each well in the ELISA plate for detection, with two replicate wells repeated, and incubated for 1.5 h at room temperature. The plate was drained by patting after 3 washes of PBST. After addition of 100 μl rabbit anti-murine Ig antibody labeled with HRP (purchased from Sigma) diluted with PBST at 1:10000, they were incubated for 1 h at room temperature. The plate was drained by patting after 3 washes of PBST. 100 μl of chromogen solution was added per well (mixing ELISA chromogen solution A and chromogen solution B according to a volume ratio of 1:1 before use) for development, and then 100 μl of 2M $H_2SO_4$ stop solution per well was added to terminate the reaction. OD values of each well were immediately measured with a microplate reader (Molecular Device) at a wavelength of 450 nm.

Example 3 Hybridoma Fusion and Screening

Hybridoma sp2/0 cells (from the National Collection of Authenticated Cell Cultures of the Chinese Academy of Sciences, deposit number TCM-18) were incubated at 37° C., in an incubator containing 5% $CO_2$, with the medium changed the day before fusion. After rush immunization of mice for 3 days, mouse splenocytes were separated for fusion. The fusion and screening methods were as follows: spleens of mice were taken, ground and washed, and then splenocytes were counted. Splenocytes and sp2/0 cells were mixed in a ratio of 10:1 and centrifuged at 1500 rpm for 7 min. The supernatant was washed and discarded. 1 ml PEG (1450) was added within 1 minute, shaked gently for 90 seconds, with 5 ml serum-free DMEM medium (purchased from Gibco) added in 2.5 minutes, 5 ml serum-free culture medium added at one time to terminate the reaction. The mixture was placed for 5 minutes, and centrifuged at 1280 rpm for 8 minutes. Cells were evenly seeded into 96-well plates with 200 μl per well at a rate of two million sp96/200 cells per 96-well plate. Firstly, the HAT medium containing hypoxanthine (H), aminopterin (A) and thymidine (T) was used for screening, with half medium changed every 4-10 days, and the medium was exchanged with HT medium on tDay 10. After 10 days, when hybridoma cells covered more than 10% of the bottom of the 96-well plate, the supernatant was taken for ELISA detection with an ELISA plate coated with hTSLP-hFc antigen. The method of ELISA detection was the same as the method described in Example 2. Positive hybridoma clones were selected and subjected to amplification culture in 24-well plates, subcloned by limiting dilution method, and hybridoma strains stably expressing the target antibodies were obtained, preserved and restored.

Example 4 Binding of Murine-Derived Anti-Human hTSLP Monoclonal Antibody to Human TSLP After the preferred murine-derived anti-human hTSLP monoclonal antibody was affinity-purified through a Protein G affinity chromatography column, the BCA method was used for the quantification. EC50 of the binding of an anti-human TSLP monoclonal antibody to hTSLP was detected using ELISA. The method for detection was as follows: recombinant human TSLP flag was diluted to 0.2 μg/ml with a coating buffer, added to a 96-well ELISA plate with a multichannel pipette by 100 μl/well and incubated at room temperature for 1.5 h. After the coating buffer was discarded, the plate was washed once with PBST, blocked with a blocking solution containing 1% BSA by 200 μl/well and incubated at room temperature for 2 h. The blocking solution was discarded and the plate was drained by patting for later use. Anti-human TSLP monoclonal antibody was 3-fold diluted with PBST containing 1% BSA at a starting concentration of 100 μg/ml for 12 concentration gradients. 100 μl antibodies diluted by the above gradients were pipetted into an ELISA plate with a multichannel pipette, with one well repeated, and incubated for 1.5 h at room temperature. The ELISA plate was washed 4 times with PBST and drained by patting on an absorbent paper.

TABLE 1

Affinity of exemplary murine-derived anti-human TSLP monoclonal antibodies to human TSLP

| Antibody No. | EC50 (ng/ml) |
|---|---|
| 26 | 2312 |
| 27 | 74.01 |
| 28 | 2407 |
| 29 | 30.56 |
| 32 | 31.73 |
| 34 | 44.44 |
| 40 | 67.05 |
| 48 | 53.63 |
| 52 | 38.24 |
| 57 | 85.2 |
| 43 | 37.51 |
| 59 | 77.39 |
| 65 | 28.83 |
| 68 | 29.68 |
| 73 | 36.15 |
| 81 | 37.7 |
| 86 | 28.65 |
| 87 | 31.01 |
| 88 | 80.7 |
| 89 | 204.6 |
| 95 | 28.41 |
| 100 | 37.83 |
| 101 | 18.89 |
| 107 | 23.18 |
| 111 | 25.05 |
| 125 | 30.11 |
| 133 | 19.15 |
| 142 | 38.38 |
| 151 | 27.95 |
| 163 | 39.38 |

100 μl of goat anti-human IgG Fc-HRP antibody was added per well (diluted 1000-fold with PBST containing 1% BSA immediately before use) and incubated for 1 h at room temperature. The ELISA plate was washed 4 times with PBST and drained by patting on an absorbent paper. 100 μl of development solution was added per well (mixing ELISA development solution A and chromogen development B according to a volume ratio of 1:1 before use). After development for 5 min, 80 μl of stop solution per well was added to terminate the reaction. OD values of each well were immediately measured with a microplate reader (Molecular Device) at a wavelength of 450 nm. GraphPad Prism6 software was used for data analysis. The results are shown in Table 1.

Example 5 Blocking of Murine-Derived Anti-Human hTSLP Monoclonal Antibody for TSLP Binding to TSLPR Recombinant human TSLPR-ECD-hFc was coated with a coating buffer at a concentration of 2 μg/ml, added to a 96-well ELISA plate with a multichannel pipette by 100 μl/well and incubated at room temperature for 1.5 h. The coating buffer was discarded and the plate was washed with PBST for one time.

TABLE 2

Blocking of exemplary murine-derived anti-human TSLP monoclonal antibodies for TSLP binding to TSLPR.

| Antibody No. | IC50 (ng/ml) |
|---|---|
| 26 | 6064 |
| 27 | 788.6 |
| 28 | 7527 |
| 29 | 115.8 |
| 32 | 121.5 |
| 34 | 178.5 |
| 40 | 277.8 |
| 48 | 198.4 |
| 52 | 179.2 |
| 57 | 283.3 |
| 43 | 187.2 |
| 59 | 344.9 |
| 65 | 114.4 |
| 68 | 141.1 |
| 73 | 224.2 |
| 81 | 201.1 |
| 86 | 184.5 |
| 87 | 150.4 |
| 88 | 378.7 |
| 89 | 695.6 |
| 95 | 124.4 |
| 100 | 167.1 |
| 101 | 94.17 |
| 107 | 178.1 |
| 111 | 118.1 |
| 125 | 188.9 |
| 133 | 161.4 |
| 142 | 217.1 |
| 151 | 171.1 |
| 163 | 212.2 |

The plate was blocked with a coating buffer containing 1% BSA by 200 μl/well, incubated at room temperature for 2 h and drained by patting for later use. TSLP murine-derived antibody was 3-fold diluted with PBST containing 1% BSA at a starting concentration of 100 g/ml for 11 concentration gradients and TSLP-flag-Biotin was added to the gradient-diluted antibody at a concentration of 2 ng/ml and incubated for 1 h at room temperature. The mixtures of above antibodies and TSLP-flag-Biotin were pipetted into an ELISA plate with a multichannel pipette, with one well repeated, and incubated for 1.5 h at room temperature. The ELISA plate was washed 2 times with PBST and drained by patting on an absorbent paper. 100 μl of Streptavidin-HRP antibody was added per well (diluted 1000-fold with PBST containing 1% BSA immediately before use) and incubated for 1 h at room temperature. The ELISA plate was washed 4 times with PBST and drained by patting on an absorbent paper. 100 μl of development solution was added per well (mixing ELISA development solution A and development solution B according to a volume ratio of 1:1 before use). After development for 5 min, 80 μl of stop solution per well was added to terminate the reaction. OD values of each well were immediately measured with a microplate reader at a wavelength of 450 nm and GraphPad Prism6 was used for data analysis. The results are shown in Table 2.

Example 6 Sequence Analysis of Murine-Derived Anti-Human hTSLP Monoclonal Antibody According to the results of Examples 4 and 5, 30 hybridoma cell lines were selected for sequence analysis of the antibodies. Total RNA of each hybridoma cell line was extracted using Trizol (purchased from Shanghai Biotechnology) and the mRNA was reverse-transcribed into cDNA using a reverse transcription kit (purchased from ABI). Primers reported in the reference were used for amplifying the genes encoding the light and heavy variable regions of murine-derived anti-human hTSLP monoclonal antibodies by PCR. Then PCR products were cloned into pGEM-T vectors for sequencing and analyzing the sequences of genes encoding variable regions. The sequences obtained in GenBank were compared and analyzed, all of which matched the characteristics of genes encoding mice IgG variable regions. The amino acid sequences of CDR regions of the preferred antibodies are shown in Tables 3 and 4.

TABLE 3

The amino acid sequences of heavy-chain CDRs for exemplary murine-derived anti-human TSLP antibodies.

| Antibody No. | HCDR1 (SEQ ID NO.) | HCDR2 (SEQ ID NO.) | HCDR3 (SEQ ID NO.) |
|---|---|---|---|
| 27 | 1 | 2 | 3 |
| 101 | 4 | 5 | 6 |
| 111 | 7 | 8 | 9 |
| 163 | 10 | 11 | 12 |

TABLE 4

The amino acid sequences of light-chain CDRs for exemplary murine-derived anti-human TSLP antibodies.

| Antibody No. | LCDR1 (SEQ ID NO.) | LCDR2 (SEQ ID NO.) | LCDR3 (SEQ ID NO.) |
|---|---|---|---|
| 27 | 13 | 14 | 15 |
| 101 | 16 | 17 | 18 |
| 111 | 19 | 20 | 21 |
| 163 | 22 | 23 | 24 |

Example 7 Humanization of Anti-Human TSLP Monoclonal Antibody

According to the results of sequence analysis, antibodies No. 27, 101, 111 and 163 were selected for the construction of chimeric antibodies and humanized antibodies. The chimeric antibodies were constructed by truncating the heavy chain variable region and the light chain variable region of murine-derived antibodies and connecting them with the light and heavy chain constant regions of human IgG1 by overlapping PCR, respectively.

According to the Kabat numbering scheme, the amino acid sequences of the light chain variable region and the heavy chain variable region of murine-derived anti-human TSLP monoclonal antibodies were analyzed and 3 CDRs and 4 FRs were determined. Taking antibody No. 163 as an example, by comparing the homology between NCBI IgBlast and human IgG germline sequence (Germline), IGHV3-23*04 was selected as the heavy chain CDR grafting template, the heavy chain CDR region of murine-derived anti-human TSLP monoclonal antibody No. 163 was grafted into the framework region of IGHV3-23*04 to construct a heavy chain CDR grafted antibody. Similarly, after comparing the homology with human IgG germline sequences, IGKV3-11*01 was selected as the light chain CDR grafting template, the light chain CDR region of murine anti-human TSLP monoclonal antibody No. 163 was grafted into the framework region of IGKV3-11'*01 to construct a light chain CDR grafted antibody. At the same time, on this basis, some amino acid positions in framework regions were reversely mutated. When performing reverse mutations, the amino acid sequences were encoded by Kabat and the positions were indicated by Kabat. Preferably, for light chain variable region sequence, A at position 43 of Kabat was reversely mutated to murine-derived S, and at the same time, I at position 58 was mutated to V. A at position 49 in the heavy chain variable region was reversely mutated to S. Above sequences of genes encoding variable regions were codon-optimized and synthesized by Sangon Biotech according to the preference characteristics of codon usage of *Cricetulus griseus*. Synthesized sequence of humanized variable region was connected with the human IgG1 constant region and this antibody was defined as the humanized antibody 163-Humanization of antibody 163 (163H).

By the same principle described above, remaining three antibodies were also humanized. Sequences of humanized antibodies are shown in Tables 5 and 6. The pTT6 vector was used to construct transient expression vectors of humanized heavy chains and light chains. Above light and heavy chains were combined to transfect and express the antibodies by HEK5E system. HEK293E cells were cultured in Free Style 293 Expression Medium (purchased from Gibco). Plasmids were transfected into the cells by PEI transfection method and cell supernatants were collected after 5 days. Each humanized monoclonal antibody was obtained after purification with Protein A.

Finally, the nucleotide sequence of gene encoding heavy chain variable region of humanized antibody No. 27 is shown in SEQ ID NO:25 and the amino acid sequence is shown in SEQ ID NO:26. The nucleotide sequence of gene encoding humanized light chain variable region is shown in SEQ ID NO:28 and the amino acid sequence is shown in SEQ ID NO:29. After connecting with the human IgG1 constant region, the final humanized heavy chain of 27H (the sequence is shown in SEQ ID NO:27) and humanized light chain of 27H (the sequence is shown in SEQ ID NO:30) were obtained.

The nucleotide sequence of gene encoding heavy chain variable region of humanized antibody No. 101 is shown in SEQ ID NO:31, and the amino acid sequence is shown in SEQ ID NO:32. The nucleotide sequence of gene encoding humanized light chain variable region is shown in SEQ ID NO:34, and the amino acid sequence is shown in SEQ ID NO:35. After connecting with the human IgG1 constant region, the final humanized heavy chain of 101H (the sequence is shown in SEQ ID NO:33) and humanized light chain of 101H (the sequence is shown in SEQ ID NO:36) were obtained.

The nucleotide sequence of gene encoding heavy chain variable region of humanized antibody No. 111 is shown in SEQ ID NO:37, and the amino acid sequence is shown in SEQ ID NO:38. The nucleotide sequence of gene encoding humanized light chain variable region is shown in SEQ ID NO:40, and the amino acid sequence is shown in SEQ ID NO:41. After connecting with the human IgG1 constant region, the final humanized heavy chain of 111H (the sequence is shown in SEQ ID NO:39) and humanized light chain of 101H (the sequence is shown in SEQ ID NO:42) were obtained.

The nucleotide sequence of gene encoding heavy chain variable region of humanized antibody No. 163 is shown in SEQ ID NO:43 and the amino acid sequence is shown in SEQ ID NO:44. The nucleotide sequence of gene encoding humanized light chain variable region is shown in SEQ ID NO:46 and the amino acid sequence is shown in SEQ ID NO:47. After connecting with the human IgG1 constant region, the final humanized heavy chain of 163H (the sequence is shown in SEQ ID NO:45) and humanized light chain of 101H (the sequence is shown in SEQ ID NO:48) were obtained.

TABLE 5

Nucleotide sequences and amino acid sequences of the heavy chain variable regions and light chain variable regions of humanized anti-human TSLP antibodies.

| Antibody No. | The nucleotide sequence of heavy chain variable region (SEQ ID NO.) | The nucleotide sequence of light chain variable region (SEQ ID NO.) | The amino acid sequence of heavy chain variable region (SEQ ID NO.) | The amino acid sequence of light chain variable region (SEQ ID NO.) |
|---|---|---|---|---|
| 27H | 25 | 28 | 26 | 29 |
| 101H | 31 | 34 | 32 | 35 |
| 111H | 37 | 40 | 38 | 41 |
| 163H | 43 | 46 | 44 | 47 |

TABLE 6

Amino acid sequences of heavy and light chains of humanized anti-human TSLP antibodies.

| Antibody No. | The amino acid sequence of heavy chain (SEQ ID NO.) | The amino acid sequence of light chain (SEQ ID NO.) |
|---|---|---|
| 27H | 27 | 30 |
| 101H | 33 | 36 |
| 111H | 39 | 42 |
| 163H | 45 | 48 |

Example 8 Humanized Anti-Human TSLP Antibody Blocks TSLP Binding to TSLPR

Humanized TSLP antibody was used to detect the blocking effect on TSLP binding to TSLPR according to the method in Example 5. The results are shown in Table 7.

TABLE 7

Humanized anti-human TSLP antibody blocks TSLP binding to TSLPR.

| Antibody No. | IC50 (ng/ml) |
|---|---|
| TEZ | 109.0 |
| 101H | 184.8 |
| 111H | 167.0 |
| 163H | 159.3 |

Example 9 Humanized Anti-Human TSLP Antibody Inhibits TSLP-Dependent STAT5 Activation Firstly, a stable BaF3 cell line co-expressed by hIL-7R and hTSLPR receptors was constructed. On this basis, pGL4.52 (purchased from Promega) was stably transferred to obtain a stable cell line of IL-7R/TSLPR-BaF3-Luc (STAT5).

IL-7R/TSLPR-BaF3-Luc (STAT5) cells in logarithmic phase were exchanged with serum-free IMDM medium and cultured overnight in a 37° C. incubator. The next day the antibody was diluted 3-fold at a starting concentration of 100 g/ml for 11 concentration gradients of 100 μl per well. Then 50 ul of 4 ng/ml TSLP-flag was added per well and incubated for half an hour. IL-7R/TSLPR-BaF3-Luc (STAT5) cells were cultured overnight with serum-free medium and centrifuged and exchanged with serum-free IMDM medium. The concentration of cells was adjusted to $1\times10^6$. After sufficiently mixing, 50 μl of cell suspensions was added per well in the above antibody solution and incubated at 37° C. for 4 h. After pipetting three times with a pipette tip and mixing sufficiently, 75 μl of the mixture was taken from each well in a detection white plate, with a replicate well. 75 μl substrate (purchased from Promega) of firefly Luciferase was added per well, placed for 20 min for reading at 560 nm. GraphPad Prism6 software was used for data analysis. The results are shown in FIG. 1. The IC50 of TEZ-1, 111H, 163H and TEZ-2 are 957.9 ng/ml, 184.4 ng/ml, 377.9 ng/ml and 853.8 ng/ml. The results indicate that the effect of the preferred antibody in inhibiting TSLP-dependent STAT5 activation is significantly better than that of the reference antibody.

Example 10 Humanized Anti-Human TSLP Antibody Inhibits the Secretion of TARC b PBMC Humanized anti-human TSLP antibody was diluted with RPMI 1640 medium containing 5% fetal bovine serum to the concentration of 80 μg/ml, 16 μg/ml and added to a 96-well cell culture plate at 50 l/well. The TSLP-flag proteins were diluted to a concentration of 10 ng/ml with RPMI 1640 medium containing 5% fetal bovine serum and added to the above 96-well cell wells containing TSLP antibodies, 50 μl/well. The plates were incubated in a 37° C. cell culture incubator for 1 h. Fresh PBMC (purchased in TPCS) was adjusted with RPMI 1640 medium containing 5% fetal bovine serum to $2\times10^6$ cells/ml and seeded into the above 96-well cell culture plate added with the antibody, 100 μl per well, with three replicate wells. The 96-well plate was incubated in a 37° C. incubator for 2 days, and then the culture supernatant was collected and detected with the Human CCL17/TARC Quantikine ELISA Kit (R&D Systems) for the content of TARC in the supernatant. The results are shown in Table 2. The results showed that the activity of the preferred antibody in inhibiting the secretion of TARC by PBMC was significantly better than that of the reference antibody.

Example 11 Affinity of Humanized Anti-Human TSLP Monoclonal Antibody to TSLP

The affinity of purified humanized antibody was detected by Biacore T200 (GE healthcare), with the reference antibody Tezepelumab as a control. Specific experimental method was: using Protein-A CM5 sensing chip (GE healthcare), FC1 (Flow cell 1) as the reference channel and FC2 (Flow cell 2) as the sample channel. Human antibodies or reference antibodies were captured in the FC2 channel, followed by injection of different concentrations of hTSLP-Flag. The condition of a cycle was: Analytes were injected for 4 min at 50 μl/min in all channels of FCs. Dissociation time was 20 min. 6M guanidine hydrochloride (Sinopharm Chemical Reagent Co., Ltd.) was injected at a rate of 10 l/min for 30 s for surface regeneration, and then Biacore T200 Evaluation Software Ver 1.0 was used to calculate the signal difference and affinity of the interaction between the signal of the captured antibody and the non-captured antibody. As shown in Table 8, the affinity of the humanized antibody 1631H to hTSLP was equivalent to that of the reference antibody Tezepelumab.

TABLE 8

Affinity of humanized anti-human TSLP to TSLP

| Antibody | Ka (1/Ms) | Kd (1/s) | KD (pM) |
|---|---|---|---|
| TEZ | 3.34E+06 | 4.36E−05 | 13.1 |
| 163H | 5.89E+06 | 3.02E−04 | 51.3 |

Conclusion: In the analyses of affinity and multiple in vitro functional activities, the antibodies of the present disclosure all exhibit consistent biological activities stronger than the reference antibody Tezepelumab.

It is understood that although the present application is described in some forms, the present application is not limited to what is shown and described in this specification. It is obvious to those skilled in the art that, without departing from the scope of the present application, various variations may be permitted to the embodiments and/or a certain feature or parameter. These changes are within the scope of the protection claimed in this application.

In accordance with 37 CFR 1.821(c)(1), the content of the Sequence Listing, entitled "Sequence Listing" and filed herewith, is incorporated by reference herein. The ASCII text file of the Sequence Listing was generated on Mar. 2, 2026 and has a size of 41,638 bytes.

What is claimed is:

1. An antibody or antigen binding fragment thereof that specifically binds to human thymic stromal lymphopoietinin (hTSLP), wherein the antibody or antigen-binding fragment thereof comprises:

(1) a HCDR1 consisting of SEQ ID NO: 1, a HCDR2 consisting of SEQ ID NO: 2, a HCDR3 consisting of SEQ ID NO: 3, a LCDR1 consisting of SEQ ID NO: 13, a LCDR2 consisting of SEQ ID NO: 14, and a LCDR3 consisting of SEQ ID NO: 15; or (2) a HCDR1 consisting of SEQ ID NO: 4, a HCDR2 consisting of SEQ ID NO: 5, a HCDR3 consisting of SEQ ID NO: 6, a LCDR1 consisting of SEQ ID NO: 16, a LCDR2 consisting of SEQ ID NO: 17, and a LCDR3 consisting of SEQ ID NO: 18; or (3) a HCDR1 consisting of SEQ ID NO: 7, a HCDR2 consisting of SEQ ID NO: 8, a HCDR3 consisting of SEQ ID NO: 9, a LCDR1 consisting of SEQ ID NO: 19, a LCDR2 consisting of SEQ ID NO: 20, and a LCDR3 consisting of SEQ ID NO: 21; or (4) a HCDR1 consisting of SEQ ID NO: 10, a HCDR2 consisting of SEQ ID NO: 11, a HCDR3 consisting of SEQ ID NO: 12, a LCDR1 consisting of SEQ ID NO: 22, a LCDR2 consisting of SEQ ID NO: 23, and a LCDR3 consisting of SEQ ID NO: 24.

2. The antibody or antigen-binding fragment thereof according to claim 1, wherein:

(a) the antibody has a heavy chain variable region with the sequence shown in SEQ ID NO: 26, and a light chain variable region with the sequence shown in SEQ ID NO:29; or (b) the antibody has a heavy chain variable region with the sequence shown in SEQ ID NO:32, and a light chain variable region with the sequence shown in SEQ ID NO: 35; or (c) the antibody has a heavy chain variable region with the sequence shown in SEQ ID NO:38, and a light chain variable region with the sequence shown in SEQ ID NO: 41; or (d) the antibody has a heavy chain variable region with the sequence shown in SEQ ID NO:44, and a light chain variable region with the sequence shown in SEQ ID NO: 47.

3. A pharmaceutical composition, which comprises the antibody or antigen-binding fragment thereof according to claim 1 and a pharmaceutically acceptable carrier.

4. A nucleotide molecule encoding the antibody or antigen-binding fragment thereof according to claim 1.

5. An expression vector, which comprises the nucleotide molecule according to claim 4.

6. A host cell, which comprises the nucleotide molecule according to claim 4 or an expression vector comprising the nucleotide molecule.

7. A method for preparing the antibody or antigen-binding fragment thereof according to claim 1, comprising: a) culturing host cells comprising a nucleotide molecule encoding the antibody or an antigen-binding fragment thereof under an expression condition that allows the host cells to produce the antibody or antigen-binding fragment thereof, thereby expressing the antibody or antigen-binding fragment thereof; and b) isolating and purifying the antibody or antigen-binding fragment thereof expressed in step a).

8. The antibody or antigen-binding fragment thereof according to claim 1, wherein the antigen-binding fragment is selected from the group consisting of Fab, Fab', F(ab')2, Fv, and scFv.

9. The pharmaceutical composition according to claim 3, wherein:

(a) the antibody has a heavy chain variable region with the sequence shown in SEQ ID NO: 26, and a light chain variable region with the sequence shown in SEQ ID NO:29; or (b) the antibody has a heavy chain variable region with the sequence shown in SEQ ID NO:32, and a light chain variable region with the sequence shown in SEQ ID NO: 35; or (c) the antibody has a heavy chain variable region with the sequence shown in SEQ ID NO:38, and a light chain variable region with the sequence shown in SEQ ID NO: 41; or (d) the antibody has a heavy chain variable region with the sequence shown in SEQ ID NO:44, and a light chain variable region with the sequence shown in SEQ ID NO: 47.

10. The nucleotide molecule according to claim 4, wherein:

(1) the nucleotide sequence of heavy chain variable region of the antibody is shown in SEQ ID NO: 25, and the nucleotide sequence of light chain variable region of the antibody is shown in SEQ ID NO: 28; or (2) the nucleotide sequence of heavy chain variable region of the antibody is shown in SEQ ID NO: 31, and the nucleotide sequence of light chain variable region of the antibody is shown in SEQ ID NO: 34; or (3) the nucleotide sequence of heavy chain variable region of the antibody is shown in SEQ ID NO: 37, and the nucleotide sequence of light chain variable region of the antibody is shown in SEQ ID NO: 40; or (4) the nucleotide sequence of heavy chain variable region of the antibody is shown in SEQ ID NO: 43, and the nucleotide sequence of light chain variable region of the antibody is shown in SEQ ID NO: 46.

11. A method for preventing or treating TSLP-related diseases, comprising administering to a subject the antibody or antigen-binding fragment thereof according to claim 1 or a pharmaceutical composition comprising the antibody or antigen-binding fragment thereof.

12. The method according to claim 11, wherein the TSLP-related diseases are immune-mediated inflammatory diseases.

13. The method according to claim 12, wherein the immune-mediated inflammatory diseases are selected from asthma, chronic obstructive pulmonary disease, atopic dermatitis, allergic rhinitis, fibrosis, inflammatory bowel disease and Hodgkin lymphoma.

14. The antibody or antigen-binding fragment thereof according to claim 1, wherein:

(1) the antibody has a heavy chain with the sequence shown in SEQ ID NO: 39, and a light chain with the sequence shown in SEQ ID NO: 42; or (2) the antibody has a heavy chain with the sequence shown in SEQ ID NO: 45, and a light chain with the sequence shown in SEQ ID NO: 48; or (3) the antibody has a heavy chain with the sequence shown in SEQ ID NO: 33, and a light chain with the sequence shown in SEQ ID NO: 36; or (4) the antibody has a heavy chain with the sequence shown in SEQ ID NO: 27, and a light chain with the sequence shown in SEQ ID NO: 30.

15. The pharmaceutical composition according to claim 3, wherein:

(I) the antibody has a heavy chain with the sequence shown in SEQ ID NO: 39, and a light chain with the sequence shown in SEQ ID NO: 42; or (II) the antibody has a heavy chain with the sequence shown in SEQ ID NO: 45, and a light chain with the sequence shown in SEQ ID NO: 48; or (III) the antibody has a heavy chain with the sequence shown in SEQ ID NO: 33, and a light chain with the sequence shown in SEQ ID NO: 36; or (IV) the antibody has a heavy chain with the sequence shown in SEQ ID NO: 27, and a light chain with the sequence shown in SEQ ID NO: 30.

* * * * *

SEQUENCE LISTING

<160> NUMBER OF SEQ ID NOS: 50

<210> SEQ ID NO 1
<211> LENGTH: 5
<212> TYPE: PRT
<213> ORGANISM: Mus musculus

<400> SEQUENCE: 1

Asn Ser Gly Val Ser
1 5

<210> SEQ ID NO 2
<211> LENGTH: 16
<212> TYPE: PRT
<213> ORGANISM: Mus musculus

<400> SEQUENCE: 2

Val Ile Trp Gly Asp Gly Ser Thr Asn Tyr His Ser Ala Leu Ile Ser
1 5 10 15

<210> SEQ ID NO 3
<211> LENGTH: 10
<212> TYPE: PRT
<213> ORGANISM: Mus musculus

<400> SEQUENCE: 3

Pro Asp Gly Tyr Ser Gly Ile Phe Ala Tyr
1 5 10

<210> SEQ ID NO 4
<211> LENGTH: 5
<212> TYPE: PRT
<213> ORGANISM: Mus musculus

<400> SEQUENCE: 4

Lys Tyr Trp Ile Gln
1 5

<210> SEQ ID NO 5
<211> LENGTH: 17
<212> TYPE: PRT

<213> ORGANISM: Mus musculus

<400> SEQUENCE: 5

Glu Ile Phe Pro Gly Thr Gly Thr Thr Tyr Tyr Asn Glu Ile Phe Lys
1 5 10 15

Ala

<210> SEQ ID NO 6
<211> LENGTH: 12
<212> TYPE: PRT
<213> ORGANISM: Mus musculus

<400> SEQUENCE: 6

Arg Gly Asp Tyr Asp Val Tyr Tyr Ala Leu Asp Tyr
1 5 10

<210> SEQ ID NO 7
<211> LENGTH: 5
<212> TYPE: PRT
<213> ORGANISM: Mus musculus

<400> SEQUENCE: 7

Tyr Ser Gly Val Asn
1 5

<210> SEQ ID NO 8
<211> LENGTH: 16
<212> TYPE: PRT
<213> ORGANISM: Mus musculus

<400> SEQUENCE: 8

Val Ile Trp Gly Asp Gly Ser Thr Asn Phe His Ser Ala Leu Ile Ser
1 5 10 15

<210> SEQ ID NO 9
<211> LENGTH: 10
<212> TYPE: PRT
<213> ORGANISM: Mus musculus

<400> SEQUENCE: 9

Pro Asp Gly Tyr Ser Gly Ile Phe Ala Tyr
1 5 10

<210> SEQ ID NO 10
<211> LENGTH: 5
<212> TYPE: PRT
<213> ORGANISM: Mus musculus

<400> SEQUENCE: 10

Ser Phe Gly Met His
1 5

<210> SEQ ID NO 11
<211> LENGTH: 17
<212> TYPE: PRT
<213> ORGANISM: Mus musculus

<400> SEQUENCE: 11

Tyr Ile Ser Ser Gly Ser Ser Asn Ile Tyr Tyr Ala Asp Thr Val Lys
1 5 10 15

Gly

<210> SEQ ID NO 12

<211> LENGTH: 13
<212> TYPE: PRT
<213> ORGANISM: Mus musculus

<400> SEQUENCE: 12

Asp Gly Gly Ser Arg Arg His Tyr Tyr Val Met Asp Tyr
1 5 10

<210> SEQ ID NO 13
<211> LENGTH: 12
<212> TYPE: PRT
<213> ORGANISM: Mus musculus

<400> SEQUENCE: 13

Ser Ala Ser Ser Ser Ile Ser Ser Asn Tyr Leu His
1 5 10

<210> SEQ ID NO 14
<211> LENGTH: 7
<212> TYPE: PRT
<213> ORGANISM: Mus musculus

<400> SEQUENCE: 14

Arg Thr Ser Asn Leu Ala Ser
1 5

<210> SEQ ID NO 15
<211> LENGTH: 9
<212> TYPE: PRT
<213> ORGANISM: Mus musculus

<400> SEQUENCE: 15

Gln Leu Gly Ser Gly Ile Leu Phe Thr
1 5

<210> SEQ ID NO 16
<211> LENGTH: 10
<212> TYPE: PRT
<213> ORGANISM: Mus musculus

<400> SEQUENCE: 16

Ser Ala Asn Ser Gly Val Asn Tyr Ile His
1 5 10

<210> SEQ ID NO 17
<211> LENGTH: 7
<212> TYPE: PRT
<213> ORGANISM: Mus musculus

<400> SEQUENCE: 17

Thr Thr Ser Asn Leu Ala Ser
1 5

<210> SEQ ID NO 18
<211> LENGTH: 9
<212> TYPE: PRT
<213> ORGANISM: Mus musculus

<400> SEQUENCE: 18

Gln Gln Arg Ser Ser Tyr Pro Phe Thr
1 5

<210> SEQ ID NO 19
<211> LENGTH: 12
<212> TYPE: PRT

<213> ORGANISM: Mus musculus

<400> SEQUENCE: 19

Ser Ala Ser Ser Ser Leu Ser Ser Asn Tyr Leu His
1 5 10

<210> SEQ ID NO 20
<211> LENGTH: 7
<212> TYPE: PRT
<213> ORGANISM: Mus musculus

<400> SEQUENCE: 20

Arg Thr Ser Asn Leu Ala Ser
1 5

<210> SEQ ID NO 21
<211> LENGTH: 9
<212> TYPE: PRT
<213> ORGANISM: Mus musculus

<400> SEQUENCE: 21

Gln Gln Gly Ser Gly Ile Leu Val Thr
1 5

<210> SEQ ID NO 22
<211> LENGTH: 11
<212> TYPE: PRT
<213> ORGANISM: Mus musculus

<400> SEQUENCE: 22

Lys Ala Ser Gln Asp Val Ser Pro Ala Val Ala
1 5 10

<210> SEQ ID NO 23
<211> LENGTH: 7
<212> TYPE: PRT
<213> ORGANISM: Mus musculus

<400> SEQUENCE: 23

Ser Ala Ser Tyr Arg Tyr Thr
1 5

<210> SEQ ID NO 24
<211> LENGTH: 9
<212> TYPE: PRT
<213> ORGANISM: Mus musculus

<400> SEQUENCE: 24

Gln Gln His Tyr Ser Ser Pro Phe Thr
1 5

<210> SEQ ID NO 25
<211> LENGTH: 354
<212> TYPE: DNA
<213> ORGANISM: Artificial Sequence
<220> FEATURE:
<223> OTHER INFORMATION: nucleotide sequence of VH

<400> SEQUENCE: 25
caggtgcagc tgcaggagtc tggccctggc ctggtgaagc cttctcagac cctgtctctg 60
acctgtaccg tgtctggctt ctctctgacc aactctggcg tgtcttgggt gagacagcct 120
cctggcaagg gcctggagtg gctgggcgtg atctggggcg atggctctac caactaccac 180
tctgccctga tctctagact gaccatctct aaggataact ctaagtctac cgtgtacctg 240

```
cagatgaact ctctgagagc cgaggatacc gccgtgtact actgtgccaa gcctgatggc    300

tactctggca tcttcgccta ctggggccag ggcaccctgg tgaccgtgtc ttct          354


<210> SEQ ID NO 26
<211> LENGTH: 118
<212> TYPE: PRT
<213> ORGANISM: Artificial Sequence
<220> FEATURE:
<223> OTHER INFORMATION: amino acide sequence of VH

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Lys Pro Asp Gly Tyr Ser Gly Ile Phe Ala Tyr Trp Gly Gln Gly Thr
            100                 105                 110

Leu Val Thr Val Ser Ser
        115


<210> SEQ ID NO 27
<211> LENGTH: 448
<212> TYPE: PRT
<213> ORGANISM: Artificial Sequence
<220> FEATURE:
<223> OTHER INFORMATION: heavy chain

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Lys Pro Asp Gly Tyr Ser Gly Ile Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 28
<211> LENGTH: 324
<212> TYPE: DNA
<213> ORGANISM: Artificial Sequence
<220> FEATURE:
<223> OTHER INFORMATION: nucleotide sequence of VL

<400> SEQUENCE: 28

gagatcgtgc tgacccagtc tcctggcacc ctgtctctgt ctcctggcga gagagccacc     60

ctgagctgtt ctgcctcttc ttctatctct tctaactacc tgcactggta ccagcagaag    120

cctggccagt ctcctagact gctgatctac agaacctcta acctggcctc tggcgtgcct    180

gatagattct ctggctctgg ctctggcacc gatttcaccc tgaccatctc tagactggag    240

cctgaggatt tcgccgtgta ctactgtcag ctgggctctg gcatcctgtt caccttcggc    300

cagggcacca agctggagat caag                                           324


<210> SEQ ID NO 29
<211> LENGTH: 108
```

```
<212> TYPE: PRT
<213> ORGANISM: Artificial Sequence
<220> FEATURE:
<223> OTHER INFORMATION: amino acid sequence of VL

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Gln Ser Pro Arg Leu Leu
        35                  40                  45

Ile Tyr Arg Thr Ser Asn Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Leu Gly Ser Gly Ile Leu
                85                  90                  95

Phe Thr Phe Gly Gln Gly Thr Lys Leu Glu Ile Lys
            100                 105


<210> SEQ ID NO 30
<211> LENGTH: 215
<212> TYPE: PRT
<213> ORGANISM: Artificial Sequence
<220> FEATURE:
<223> OTHER INFORMATION: light chain

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Gln Ser Pro Arg Leu Leu
        35                  40                  45

Ile Tyr Arg Thr Ser Asn Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Leu Gly Ser Gly Ile Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 31
<211> LENGTH: 363
<212> TYPE: DNA
<213> ORGANISM: Artificial Sequence
<220> FEATURE:
<223> OTHER INFORMATION: nucleotide sequence of VH

<400> SEQUENCE: 31
caggtgcagc tggtgcagtc tggcgccgag gtgaagaagc ctggcgcctc tgtgaaggtg 60
tcttgtaaga cctctggcta caccttcacc aagtactgga tccagtgggt gagacaggcc 120
cctggccagg gcctggagtg gatcggcgag atcttccctg gcaccggcac cacctactac 180
aacgagatct tcaaggccag agtgaccctg accgtggata cctctacctc taccgcctac 240
atggagctgt ctagcctgag atctgaggat accgccgtgt actactgtgc cagaagaggc 300
gattacgatg tgtactacgc cctggattac tggggccagg gcaccctggt gaccgtgtct 360
tct 363

<210> SEQ ID NO 32
<211> LENGTH: 121
<212> TYPE: PRT
<213> ORGANISM: Artificial Sequence
<220> FEATURE:
<223> OTHER INFORMATION: amino acid sequence of VH

<400> SEQUENCE: 32

Gln Val Gln Leu Val Gln Ser Gly Ala Glu Val Lys Lys Pro Gly Ala
1 5 10 15

Ser Val Lys Val Ser Cys Lys Thr Ser Gly Tyr Thr Phe Thr Lys Tyr
20 25 30

Trp Ile Gln Trp Val Arg Gln Ala Pro Gly Gln Gly Leu Glu Trp Ile
35 40 45

Gly Glu Ile Phe Pro Gly Thr Gly Thr Thr Tyr Tyr Asn Glu Ile Phe
50 55 60

Lys Ala Arg Val Thr Leu Thr Val Asp Thr Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Arg Gly Asp Tyr Asp Val Tyr Tyr Ala Leu Asp Tyr Trp Gly
100 105 110

Gln Gly Thr Leu Val Thr Val Ser Ser
115 120

<210> SEQ ID NO 33
<211> LENGTH: 451
<212> TYPE: PRT
<213> ORGANISM: Artificial Sequence
<220> FEATURE:
<223> OTHER INFORMATION: heavy chain

<400> SEQUENCE: 33

Gln Val Gln Leu Val Gln Ser Gly Ala Glu Val Lys Lys Pro Gly Ala
1 5 10 15

Ser Val Lys Val Ser Cys Lys Thr Ser Gly Tyr Thr Phe Thr Lys Tyr
20 25 30

Trp Ile Gln Trp Val Arg Gln Ala Pro Gly Gln Gly Leu Glu Trp Ile
35 40 45

Gly Glu Ile Phe Pro Gly Thr Gly Thr Thr Tyr Tyr Asn Glu Ile Phe

```
    50                  55                  60

Lys Ala Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asp Tyr Asp Val Tyr Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 34
```

```
<211> LENGTH: 318
<212> TYPE: DNA
<213> ORGANISM: Artificial Sequence
<220> FEATURE:
<223> OTHER INFORMATION: nucleotide sequence of VL

<400> SEQUENCE: 34

gagatcgtgc tgacccagtc tcctgccacc ctgtctctgt ctcctggcga gagagccacc     60

ctgtcttgtt ctgccaactc tggcgtgaac tacatccact ggtaccagca gaagcctggc    120

caggccccta gattctggat ctggaccacc tctaacctgg cctctggcgt gcctgccaga    180

ttctctggct ctggctctgg caccgatttc accctgacca tctctagcct ggagcctgag    240

gatttcgccg tgtactactg tcagcagaga tcttcttacc ctttcacctt cggccagggc    300

accaagctgg agatcaag                                                  318


<210> SEQ ID NO 35
<211> LENGTH: 106
<212> TYPE: PRT
<213> ORGANISM: Artificial Sequence
<220> FEATURE:
<223> OTHER INFORMATION: amino acid sequence of VL

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Ser Ala Asn Ser Gly Val Asn Tyr Ile
            20                  25                  30

His Trp Tyr Gln Gln Lys Pro Gly Gln Ala Pro Arg Phe Trp Ile Trp
        35                  40                  45

Thr Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Gln Gly Thr Lys Leu Glu Ile Lys
            100                 105


<210> SEQ ID NO 36
<211> LENGTH: 213
<212> TYPE: PRT
<213> ORGANISM: Artificial Sequence
<220> FEATURE:
<223> OTHER INFORMATION: light chain

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Ser Ala Asn Ser Gly Val Asn Tyr Ile
            20                  25                  30

His Trp Tyr Gln Gln Lys Pro Gly Gln Ala Pro Arg Phe Trp Ile Trp
        35                  40                  45

Thr Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95
```

```
Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 37
<211> LENGTH: 354
<212> TYPE: DNA
<213> ORGANISM: Artificial Sequence
<220> FEATURE:
<223> OTHER INFORMATION: nucleotide sequence of VH

<400> SEQUENCE: 37

gaggtgcagc tggtggagtc cggcggcgga ctggtgcagc ctggaggaag cctgcggctg      60

agctgctccg tgagcggctt tagcctgacc tacagcggcg tgaattgggt gaggcaggct     120

cccggcaagg gcctggagtg gctgggagca atctggggcg atggcagcac caactaccac     180

tccgccctga tcagccggct gaccatctcc aaggacaaca gcaagtccac cgtgtacctg     240

cagatgaaca gcctgagggc cgaggacacc gccgtgtatt attgcgctaa gcccgatggc     300

tattccggca tctttgccta ctggggccag ggcaccctgg tgaccgtgtc ctcc           354


<210> SEQ ID NO 38
<211> LENGTH: 118
<212> TYPE: PRT
<213> ORGANISM: Artificial Sequence
<220> FEATURE:
<223> OTHER INFORMATION: amino acid sequence of VH

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ser Val Ser Gly Phe Ser Leu Thr Tyr Ser
            20                  25                  30

Gly Val Asn Trp Val Arg Gln Ala Pro Gly Lys Gly Leu Glu Trp Leu
        35                  40                  45

Gly Ala Ile Trp Gly Asp Gly Ser Thr Asn Tyr His Ser Ala Leu Ile
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Lys Pro Asp Gly Tyr Ser Gly Ile Phe Ala Tyr Trp Gly Gln Gly Thr
            100                 105                 110

Leu Val Thr Val Ser Ser
        115
```

<210> SEQ ID NO 39
<211> LENGTH: 448
<212> TYPE: PRT
<213> ORGANISM: Artificial Sequence
<220> FEATURE:
<223> OTHER INFORMATION: heavy chain

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ser Val Ser Gly Phe Ser Leu Thr Tyr Ser
            20                  25                  30

Gly Val Asn Trp Val Arg Gln Ala Pro Gly Lys Gly Leu Glu Trp Leu
        35                  40                  45

Gly Ala Ile Trp Gly Asp Gly Ser Thr Asn Tyr His Ser Ala Leu Ile
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Lys Pro Asp Gly Tyr Ser Gly Ile Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 40
<211> LENGTH: 324
<212> TYPE: DNA
<213> ORGANISM: Artificial Sequence
<220> FEATURE:
<223> OTHER INFORMATION: nucleotide sequence of VL

<400> SEQUENCE: 40

```
gagatcgtgc tgacccagtc ccctggcacc ctgagcctga gccccggaga gagagctacc     60

ctgagctgca gcgcaagcag ctccctgagc tccaattacc tgcactggta tcagcagaag    120

cctggccagg ctcccaggct gctgatctac aggaccagca acctggccag cggcgtgcct    180

gaccggtttt ccggctccgg ctccggaacc gatttcaccc tgaccatctc caggctggag    240

cccgaggact ttgccgtgta ctattgtcag cagggctccg gcatcctggt gaccttcggc    300

cagggcacca agctggagat caag                                           324
```

<210> SEQ ID NO 41
<211> LENGTH: 108
<212> TYPE: PRT
<213> ORGANISM: Artificial Sequence
<220> FEATURE:
<223> OTHER INFORMATION: amino acid sequence of VL

<400> SEQUENCE: 41

```
Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Leu Ser Ser Asn
            20                  25                  30

Tyr Leu His Trp Tyr Gln Gln Lys Pro Gly Gln Ala Pro Arg Leu Leu
        35                  40                  45

Ile Tyr Arg Thr Ser Asn Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Gly Ile Leu
                85                  90                  95

Val Thr Phe Gly Gln Gly Thr Lys Leu Glu Ile Lys
            100                 105
```

<210> SEQ ID NO 42
<211> LENGTH: 215
<212> TYPE: PRT
<213> ORGANISM: Artificial Sequence
<220> FEATURE:
<223> OTHER INFORMATION: light chain

<400> SEQUENCE: 42

Glu Ile Val Leu Thr Gln Ser Pro Gly Thr Leu Ser Leu Ser Pro Gly
1 5 10 15

Glu Arg Ala Thr Leu Ser Cys Ser Ala Ser Ser Ser Leu Ser Ser Asn
20 25 30

Tyr Leu His Trp Tyr Gln Gln Lys Pro Gly Gln Ala Pro Arg Leu Leu
35 40 45

Ile Tyr Arg Thr Ser Asn Leu Ala Ser Gly Val Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Ser Gly Ile Leu
85 90 95

Val Thr Phe Gly Gln Gly Thr Lys Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 43
<211> LENGTH: 366
<212> TYPE: DNA
<213> ORGANISM: Artificial Sequence
<220> FEATURE:
<223> OTHER INFORMATION: nucleotide sequence of VH

<400> SEQUENCE: 43
gaagtgcagc tggtggagtc tggcggcggc ctggtgcagc ctggcggctc tctgagactg 60
tcttgtgccg cctctggctt caccttctct tctttcggca tgcactgggt gagacaggcc 120
cctggcaagg gcctggagtg ggtgtcctac atctcttctg gctcttctaa catctactac 180
gccgataccg tgaagggcag attcaccatc tctagagata acgccaagaa ctctctgtac 240
ctgcagatga actctctgag agccgaggat accgccgtgt actactgtgc cagagatggc 300
ggctctagaa gacactacta cgtgatggat tactggggcc agggcaccct ggtgaccgtg 360
tcttct 366

<210> SEQ ID NO 44
<211> LENGTH: 122
<212> TYPE: PRT
<213> ORGANISM: Artificial Sequence
<220> FEATURE:
<223> OTHER INFORMATION: amino acid sequence of VH

<400> SEQUENCE: 44

Glu Val Gln Leu Val Glu Ser Gly Gly Gly Leu Val Gln Pro Gly Gly
1 5 10 15

```
Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ser Tyr Ile Ser Ser Gly Ser Ser Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Ser Arg Arg His Tyr Tyr Val Met Asp Tyr Trp
            100                 105                 110

Gly Gln Gly Thr Leu Val Thr Val Ser Ser
        115                 120


<210> SEQ ID NO 45
<211> LENGTH: 452
<212> TYPE: PRT
<213> ORGANISM: Artificial Sequence
<220> FEATURE:
<223> OTHER INFORMATION: heavy chain

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ser Tyr Ile Ser Ser Gly Ser Ser Asn Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Ser Arg Arg His Tyr Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 46
<211> LENGTH: 321
<212> TYPE: DNA
<213> ORGANISM: Artificial Sequence
<220> FEATURE:
<223> OTHER INFORMATION: nucleotide sequence of VL

<400> SEQUENCE: 46

gagatcgtgc tgacccagtc tcctgccacc ctgagcctgt ctcctggcga gagagccacc      60

ctgtcttgta aggcctctca ggatgtgtct cctgccgtgg cctggtacca gcagaagcct     120

ggccagtccc ctagactgct gatctactct gcctcttaca gatacaccgg cgtgcctgcc     180

agattctctg gcagcggctc tggcaccgat ttcaccctga ccatctctag cctggagcct     240

gaggatttcg ccgtgtacta ctgtcagcag cactacagct ctcctttcac cttcggccag     300

ggcaccaagc tggagatcaa g                                               321


<210> SEQ ID NO 47
<211> LENGTH: 107
<212> TYPE: PRT
<213> ORGANISM: Artificial Sequence
<220> FEATURE:
<223> OTHER INFORMATION: amino acid sequence of VL

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asp Val Ser Pro Ala
            20                  25                  30

Val Ala Trp Tyr Gln Gln Lys Pro Gly Gln Ser Pro Arg Leu Leu Ile
        35                  40                  45
```

```
Tyr Ser Ala Ser Tyr Arg Tyr Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Tyr Ser Ser Pro Phe
                85                  90                  95

Thr Phe Gly Gln Gly Thr Lys Leu Glu Ile Lys
            100                 105


<210> SEQ ID NO 48
<211> LENGTH: 214
<212> TYPE: PRT
<213> ORGANISM: Artificial Sequence
<220> FEATURE:
<223> OTHER INFORMATION: light chain

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asp Val Ser Pro Ala
            20                  25                  30

Val Ala Trp Tyr Gln Gln Lys Pro Gly Gln Ser Pro Arg Leu Leu Ile
        35                  40                  45

Tyr Ser Ala Ser Tyr Arg Tyr Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Tyr Ser Ser Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 49
<211> LENGTH: 16
<212> TYPE: PRT
<213> ORGANISM: Artificial Sequence
<220> FEATURE:
<223> OTHER INFORMATION: HCDR2 sequence

<400> SEQUENCE: 49

Ala Ile Trp Gly Asp Gly Ser Thr Asn Tyr His Ser Ala Leu Ile Ser
1               5                   10                  15
```

-continued

```
<210> SEQ ID NO 50
<211> LENGTH: 8
<212> TYPE: PRT
<213> ORGANISM: Artificial Sequence
<220> FEATURE:
<223> OTHER INFORMATION: Flag tag

<400> SEQUENCE: 50

Asp Tyr Lys Asp Asp Asp Asp Lys
1               5
```